United States Patent [19]
Rozzi et al.

[11] Patent Number: 5,607,663
[45] Date of Patent: Mar. 4, 1997

[54] HYDROCARBYL CONTAINING COATINGS, COMPOSITIONS AND METHODS OF USE

[75] Inventors: Sharon M. Rozzi, West Lakeland Township; Sumita B. Mitra, West St. Paul; Brant L. Kedrowski, Minneapolis; Charles E. Shelburne, Brooklyn Park, all of Minn.

[73] Assignee: Minnesota Mining and Manufacturing Company, St. Paul, Minn.

[21] Appl. No.: 348,048

[22] Filed: Dec. 1, 1994

[51] Int. Cl.$^6$ ...................................................... A61K 7/16
[52] U.S. Cl. ................................................................ 424/49
[58] Field of Search ................................................. 424/49

[56] References Cited

U.S. PATENT DOCUMENTS

| | | |
|---|---|---|
| 4,161,518 | 7/1979 | Wen et al. . |
| 4,663,202 | 5/1987 | Causton . |
| 4,693,935 | 9/1987 | Mazurek . |
| 4,728,571 | 3/1988 | Clemens et al. . |
| 4,748,198 | 5/1988 | Takahashi et al. . |
| 4,872,936 | 10/1989 | Engelbrecht . |
| 4,950,479 | 8/1990 | Hill et al. . |
| 4,963,347 | 10/1990 | Humphries et al. . |
| 4,972,037 | 11/1990 | Garbe et al. . |
| 4,981,902 | 1/1991 | Mitra et al. . |
| 4,981,903 | 1/1991 | Garbe et al. . |
| 5,021,477 | 6/1991 | Garbe et al. . |
| 5,078,988 | 1/1992 | Lin et al. . |
| 5,154,762 | 10/1992 | Mitra et al. . |
| 5,188,822 | 2/1993 | Viccaro et al. . |
| 5,336,728 | 8/1994 | Humphries et al. . |

FOREIGN PATENT DOCUMENTS

| | | |
|---|---|---|
| 0142172 | 5/1985 | European Pat. Off. . |
| 0412770 | 2/1991 | European Pat. Off. . |
| 0412771 | 2/1991 | European Pat. Off. . |
| WO91/13608 | 3/1991 | WIPO . |
| WO95/15740 | 6/1995 | WIPO . |

OTHER PUBLICATIONS

A. Gaffar, J. Afflitto, N. Nuran, "Toothbrush Chemistry" Am. Chem. Soc. (Jul. 1993).

*Primary Examiner*—Paul J. Killos
*Attorney, Agent, or Firm*—Gary L. Griswold; Walter N. Kirn; Dale A. Bjorkman

[57] ABSTRACT

Coatings for hard tissue and surfaces of the oral environment are provided that reduce adhesion of bacteria and proteinaceous substances to these surfaces. Methods of reducing adhesion of these materials to such surfaces, and polymers for incorporation into such coatings are also provided.

33 Claims, No Drawings

HYDROCARBYL CONTAINING COATINGS, COMPOSITIONS AND METHODS OF USE

FIELD OF THE INVENTION

This invention relates to coatings on hard tissue surfaces or surfaces of the oral environment. More specifically, this invention relates to substantive coatings for hard tissue surfaces or surfaces of the oral environment.

BACKGROUND OF THE INVENTION

Plaque is a common factor in caries, gum disease and discoloration of teeth and greatly contributes to their development. Plaque is initiated when cariogenic bacteria adhere to pellicle, a proteinaceous film on the surface of teeth. Plaque, in turn, acts as a nucleus for the formation of calculus. As calculus matures and hardens it tends to stain due to the absorption of dietary chromagens. Additionally, oral restorative materials may be inherently susceptible to build-up of stain from dietary chromagens. It is desirable to have a means to avoid stain absorption and adherence of bacteria to hard tissue and surfaces of the oral environment.

U.S. Pat. No. 5,078,988 to Lin et al. discloses dentifrices including modified aminoalkyl silicones. The modified silicones are said to form a hydrophobic layer on the teeth for prevention of caries and stain. PCT patent application number WO 91/13608 to Rolla et al. discloses dentifrices comprising a liquid silicone oil and a fat-soluble antibacterial agent, which is described as being useful for protection of teeth against plaque formation due to a slow release of antibacterial agent into the saliva.

SUMMARY OF THE INVENTION

The present invention provides coatings on hard tissue surfaces or surfaces of the oral environment, which coating comprises a polymer comprising repeating units A) 1–80% by weight of a polar or polarizable group
B) 0–98 % by weight of a modulating group
C) 1–40% by weight of a hydrophobic hydrocarbon moiety having a weight average molecular weight greater than about 160, wherein said coating has a Wilhelmy Balance Test Advancing Contact Angle greater than 55°.

The present invention also provides dental compositions suitable for coating human oral surfaces comprising a polymer comprising repeating units A) 1–80% by weight of a polar or polarizable group
B) 0–98 % by weight of a modulating group
C) 1–40% by weight of a hydrophobic hydrocarbon moiety having a weight average molecular weight greater than about 160, wherein said coating has a Wilhelmy Balance Test Advancing Contact Angle greater than 55°, wherein said polymer additionally contains at least one silane moiety that is capable of undergoing a condensation reaction.

These compositions optionally may also comprise catalysts to promote the silane condensation reaction, and optionally an additional compound comprising at least two condensation silicone reaction sites that are capable of undergoing a condensation reaction. This additional compound acts as a bridging compound between the polymers described above after completion of the condensation reaction.

Additionally, it has surprisingly been found that significant enhancement of resistance to stain and bacterial adhesion may be provided by treatment of surfaces having the above coating with a surfactant.

The present invention also provides in another embodiment polymers for coating hard tissue surfaces or surfaces of the oral environment that are crosslinkable on the surface.

In yet another embodiment, dental devices are provided that have a coating comprising the polymer system as noted above.

DETAILED DESCRIPTION

This invention relates to coatings on hard tissues such as dentin, enamel, cementum and bone. Alternatively, the coating may be provided on other surfaces of the oral environment, including surfaces of dental restorations, orthodontic devices or prostodontic devices. Dental restorations include restorations fabricated from resin-based composites, amalgam, glass ionomers, ceramics and a variety of hybrid materials derived from these. Orthodontic devices include orthodontic brackets, wires and the like. Prostodontic devices include dental bridges, crowns, dentures, and the like.

The coatings are provided in an amount sufficient to provide resistance of the coated surface to bacterial adhesion, plaque formation or staining from foods or dyes. The coating may be provided as a continuous or semi-continuous layer. Preferably, the coating is applied in an amount at least sufficient to provide a substantially continuous monolayer of polymer as described herein on the coated surface.

The coatings provided in accordance with the invention are highly substantive to the aforementioned surfaces. The coatings have low frictional coefficients and have high resistance to plaque, bacteria, food stains and the like.

It has surprisingly further been discovered that when a surface having a coating as described herein is treated with a composition comprising a surfactant, enhanced resistance to adhesion of bacteria and proteinaceous substances on the surface is observed. The surfactant-treatment step provides this surprising benefit even if the coated surface is exposed to bacteria and proteinaceous substances before the surfactant-treatment step. Thus, a coating as described herein that has been treated with a surfactant-containing composition is apparently physically different from coatings that have not been treated with a surfactant-containing composition.

The surfactant treatment can be applied (i) as part of the initial coating (ii) subsequent to initial coating, but before exposing the coated surface to undesirable oral organisms of proteinaceous substances, or (iii) after exposing the coated surface to bacteria and the like. In the last case, the surfactant treatment can be reapplied from time to time.

The coating of the present invention comprises a vinylic copolymer having repeat units of A, B and C, where A is derived from an ethylenically unsaturated monomer containing at least one polar or polarizable group, B is derived from an ethylenically unsaturated monomer optionally containing modifying groups and C is derived from an ethylenically unsaturated hydrocarbon moiety having a weight average molecular weight greater than about 160. Preferably, the polymer is less than 0.1% soluble in water.

More specifically, the unit A is derived from vinylic monomers such as acrylates, methacrylates, crotonates, itaconates and the like. The polar groups can be acidic, basic or salt. These groups can also be ionic or neutral.

Examples of polar or polarizable groups include neutral groups such as hydroxy, thio, substituted and unsubstituted amido, cyclic ethers (such as oxanes, oxetanes, furans and pyrans), basic groups (such as phosphines and amines, including primary, secondary, tertiary amines), acidic groups (such as oxy acids, and thiooxyacids of C, S, P, B) and ionic groups (such as quarternary ammonium, carboxylate salt, sulfonic acid salt and the like) and the precursors and protected forms of these groups. Additionally, A could be a macromonomer. More specific examples of such groups follow.

The A units may be derived from mono- or multifunctional carboxyl group containing molecules represented by the general formula:

$$CH_2=CR^2G-(COOH)_d$$

where $R^2$=H, methyl, ethyl, cyano, carboxy or carboxymethyl, d=1–5 and G is a bond or a hydrocarbyl radical linking group containing from 1–12 carbon atoms of valence d+1 and optionally substituted with and/or interrupted with a substituted or unsubstituted heteroatom (such as O, S, N and P). Optionally, this unit may be provided in its salt form. The preferred monomers in this class are acrylic acid, methacrylic acid, itaconic acid and N-acryloyl glycine.

The A units may, for example, be derived from mono- or multifunctional hydroxy group containing molecules represented by the general formula:

$$CH_2=CR^2-CO-L-R^3-(OH)_d$$

where $R^2$=H, methyl, ethyl, cyano, carboxy or carboxyalkyl, L=O, NH, d=1–5 and $R^3$ is a hydrocarbyl radical of valence d+1 containing from 1–12 carbon atoms. The preferred monomers in this class are hydroxyethyl (meth)acrylate, hydroxypropyl (meth)acrylate, hydroxybutyl (meth)acrylate, glycerol mono(meth)acrylate, tris(hydroxymethyl) ethane monoacrylate, pentaerythritol mono(meth)acrylate, N-hydroxymethyl (meth)acrylamide, hydroxyethyl (meth) acrylamide and hydroxypropyl (meth)acrylamide.

The A unit may alternatively be derived from mono- or multifunctional amino group containing molecules of the general formula:

$$CH_2=CR^2-CO-L-R^3-(NR^4R^5)_d$$

where $R^2$, L, $R^3$, and d are as defined above and $R^4$ and $R^5$ are H or alkyl groups of 1–12 carbon atoms or together they constitute a carbocyclic or heterocyclic group. Preferred monomers of this class are aminoethyl (meth)acrylate, aminopropyl (meth)acrylate, N,N-dimethylaminoethyl (meth) acrylate, N,N-diethylaminoethyl (meth)acrylate, N,N-dimethylaminopropyl (meth)acrylamide, N-isopropylaminopropyl (meth)acrylamide and 4-methyl-1-acryloyl-piperazine.

The A unit may also be derived from alkoxy substituted (meth)acrylates or (meth)acrylamides such as methoxyethyl (meth)acrylate, 2(2-ethoxyethoxy)ethyl (meth)acrylate, polyethylene glycol mono(meth)acrylate or polypropylene glycol mono(meth)acrylate.

A units may be derived from substituted or unsubstituted ammonium monomers of the general formula:

$$CH_2=CR^2-CO-L-R^3-(N^{\oplus}R^4R^5R^6)_dQ^-$$

where $R^2$, $R^3$, $R^4$, $R^5$, L and d are as defined above, and where $R^6$ is H or alkyl of 1–12 carbon atoms and $Q^-$ is an organic or inorganic anion. Preferred examples of such monomers are 2-N,N,N-trimethylammonium ethyl (meth)acrylate, 2-N,N,N-triethylammonium ethyl (meth)acrylate, 3-N,N,N-trimethylammonium propyl (meth)acrylate, N(2-N',N',N'-trimethylammonium) ethyl (meth)acrylamide, N-(dimethyl hydroxyethyl ammonium) propyl (meth)acrylamide etc. where the counterion may be fluoride, chloride, bromide, acetate, propionate, laurate, palmitate, stearate etc. The monomer can also be N,N-dimethyl diallyl ammonium salt of an organic or inorganic counterion.

Ammonium group containing polymers can also be prepared by using as the A unit any of the amino group containing monomer described above, and acidifying the resultant polymers with organic or inorganic acid to a pH where the pendant amino groups are substantially protonated. Totally substituted ammonium group containing polymers may be prepared by alkylating the above described amino polymers with alkylating groups, the method being commonly known in the art as the Menschutkin reaction.

The A unit of the invention can also be derived from sulfonic acid group containing monomers, such as vinyl sulfonic acid, styrene sulfonic acid, 2-acrylamido-2-methyl propane sulfonic acid, allyloxybenzene sulfonic acid, and the like. Alternatively, the A unit may be derived from phosphorous acid or boron acid group-containing monomers. These monomers may be used in the protonated acid form as monomers and the corresponding polymers obtained may be neutralized with an organic or inorganic base to give the salt form of the polymers.

The unit B is derived from acrylate or methacrylate or other vinyl polymerizable starting monomers and optionally contains functionalities that modulate properties such as glass transition temperature, solubility in the carrier medium, hydrophilic-hydrophobic balance and the like.

Examples of unit B monomers include the lower to intermediate methacrylic acid esters of 1–12 carbon straight, branched or cyclic alcohols. Other examples of B unit monomers include styrene, vinyl esters, vinyl chloride, vinylidene chloride, acryloyl monomers and the like.

Further examples of B monomers are acrylic or methacrylic acid esters of 1, 1-dihydroperfluoroalkanols (1) and homologs (2),

| | | |
|---|---|---|
| $CF_3(CF_2)_xCH_2OH$ | where x is to 20 and y is at least 1 up to 10 | (1) |
| $CF_3(CF_2)_x(CH_2)_yOH$ | | (2) |

ω-hydrofluoroalkanols 3,

| | | |
|---|---|---|
| $HCF_2(CF_2)_x(CH_2)_yOH$ | where x is 0 to 20 and y is at least 1 up to 10 | (3) | fluoroalkylsulfonamido alcohols 4, (4)

$$CF_3(CF_2)_xSO_2N\begin{matrix}R^1\\ \\CH_2CH_2OH\end{matrix}$$

where x is zero to 20 and $R^1$ is alkyl or arylalkyl of up to 20 carbon atoms or cycloalkyl of up to 6 ring carbon atoms cyclic fluoroalkyl alcohols 5, (5)

$$(CF_2)_z\begin{matrix}CF_2\\ \\CF_2\end{matrix}CF(CH_2)_yOH$$

where z is zero to 7 and y is at least 1 up to 10

| | | |
|---|---|---|
| $CF_3(CF_2CF_2-O)_q(CF_2O)_x(CH_2)_yOH$ | where q is 2 to 20 and greater than x, x is 0 to 20, and y is at least 1 up to 10 | (6) |

-continued

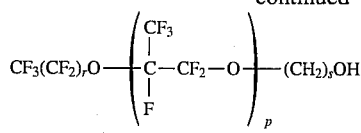

where p and s are at least 1 and r is 1 to 6.

Preferred polymerized B monomer backbone compositions include polymers of fluoroacrylates 8–13.

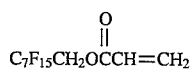 (8)

 (9)

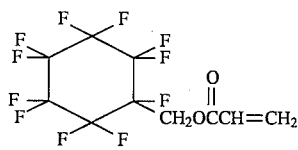 (10)

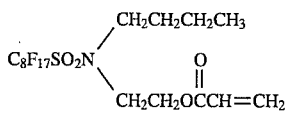 (11)

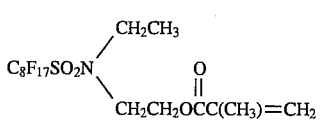 (12)

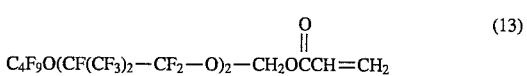 (13)

The unit C is derived from an ethylenically unsaturated preformed hydrocarbon moiety having a weight average molecular weight greater than about 160. Preferably, the hydrocarbon moiety has a molecular weight between about 160 and 100,000, and more preferably between about 160 and 20,000. The hydrocarbon moiety may be aromatic or non aromatic in nature, and optionally may contain partially or fully saturated rings. Preferred C groups are dodecyl and octadecyl acrylates and methacrylates. Other preferred C groups include macromonomers of the desired molecular weights prepared from polymerizable hydrocarbons, such as ethylene, styrene ∝-methyl styrene, vinyltoluene and methyl methacrylate.

The copolymer used in this invention is conveniently prepared by copolymerizing the starting monomer units A, B and C by standard polymerizing techniques.

The polymer may also contain one or more crosslinkable groups for later fixing of the coating or surface composition by a subsequent crosslinking reaction after the polymer has been placed on the intended substrate. Copolymers where the group B contains a crosslinkable group can be prepared by reacting an electrophilic or nucleophilic moiety of the copolymer with another compound containing the appropriate reactive group and at least one crosslinkable group, such as an ethylenic group or an epoxy group. The electrophilic or nucleophilic moiety can in some cases be the same as that present in unit A of the copolymer.

The present invention therefore also contemplates new polymers comprising repeating units A) 1–80% by weight of a polar or polarizable group B) 0–98 % by weight of a modulating group C) 1–40% by weight of a hydrophobic hydrocarbon moiety having a weight average molecular weight greater than about 160, wherein the polymer additionally comprises pendent crosslinkable groups.

The crosslinkable group is capable of undergoing a free-radical or cationic crosslinking reaction. Suitable crosslinkable groups include, but are not limited to, polymerizable ethylenically unsaturated groups and polymerizable epoxy groups. Ethylenically unsaturated groups are preferred, especially those that can be polymerized by means of a free-radical mechanism, examples of which are substituted and unsubstituted acrylates, methyacrylates, alkenes and acrylamides. In aqueous systems, polymerizable groups that are polymerized by a cationic mechanism, e.g., polymerizable ethylenically unsaturated groups such as vinyl ether groups and polymerizable epoxy groups, are less preferred since a free-radical mechanism is typically easier to employ in such systems than a cationic mechanism.

Crosslinkable polymers can be prepared according to a variety of synthetic routes, including, but not limited to reacting a polymer having electrophilic or neucleophilic groups with less than an one equivalent of a suitable compound in order to form pendent crosslinkable groups, thereby leaving electrophilic or neucleophilic groups unreacted. Alternatively, the appropriate monomers may be copolymerized with a pendent crosslinkable group already present in the monomer. The reaction in this process must be carefully controlled to avoid complete reaction of all groups in the polymerization stage, or the reaction used to form the polymer must be different from the reaction used to form crosslinks between the polymers.

The first synthetic route described above for making the crosslinkable polymer can presently be carried out by the use of a "coupling compound", i.e., a compound containing both a pendent crosslinkable group and a reactive group capable of reacting with the polymer through a functionality existing on a starting material polymer in order to form a covalent bond between the coupling compound and the electrophilic or neucleophilic group, thereby linking the pendent crosslinking group to the backbone of the polymer. Suitable coupling compounds are organic compounds, optionally containing non-interfering substituents and/or non-interfering linking groups between the pendent crosslinking group and the reactive group.

Coupling compounds suitable for use for preparing polymers of the present invention include compounds that contain at least one group capable of reacting with a polar group in order to form a covalent bond, as well as at least one polymerizable ethylenically unsaturated group. When the polar group is carboxyl, a number of groups are capable of reacting with it, including both electrophilic and nucleophilic groups. Examples of such groups include the following moieties, and groups containing these moieties: -OH, -NH$_2$, -NCO, -COCl, and

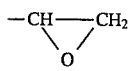

When the attaching site is an alcohol, a number of groups are capable of reacting with the alcohol. Examples of such groups include the following moieties, and groups containing these moieties: -NCO, -COCl,

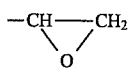

Examples of suitable coupling compounds to attach crosslinkable groups include, for example, acryloyl chloride, methacryloyl chloride, vinyl azalactone, allyl isocyanate, 2-hydroxyethylmethacrylate, 2-aminoethylmethacrylate, and 2-isocyanatoethylmethacrylate. Other examples of suitable coupling compounds include those described in U.S. Pat. No. 4,035,321. Examples of preferred coupling compounds include, for example, the following methacrylate compounds and their corresponding acrylates:

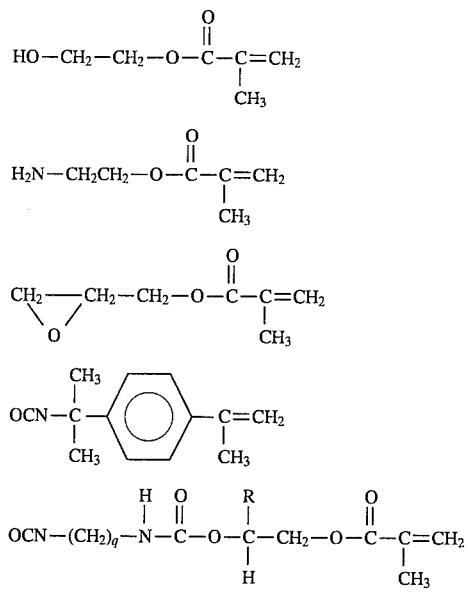

the following allyl compound:

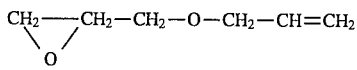

Particularly preferred coupling compounds are the following methacrylate compounds and their corresponding acrylates, wherein R and q are as defined above.

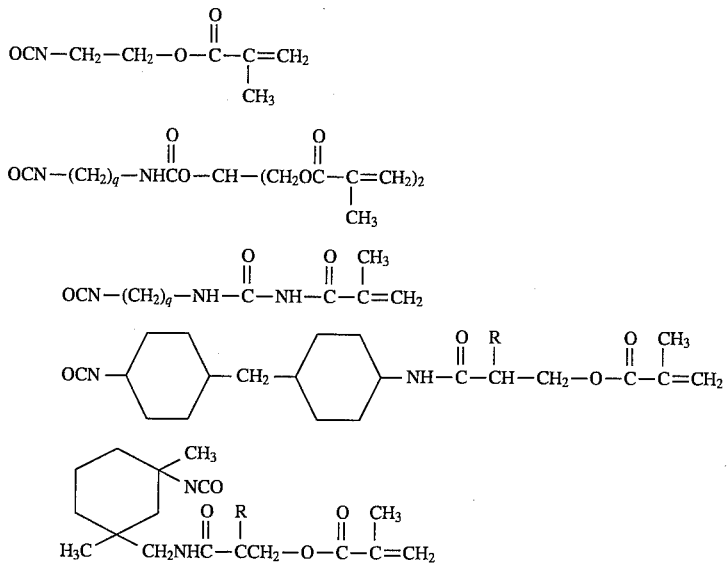

The polymer of the present invention may optionally additionally contain at least one silane moiety that is capable of undergoing a condensation reaction. A condensation reaction is the reaction of two molecules to combine, with the elimination of a third compound. The third compound may be water or, depending on the structure of the specific reactants, this third compound may be an alcohol, amine or any other such compound that is eliminated in the reaction. This silane moiety may, for example, be provided at the time of manufacture of the polymer by coreaction of the A, B and C units described above with a D unit, which is derived from an ethylenically unsaturated monomer copolymerizable with the monomers for A, B and C. This unit has a general formula

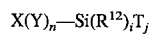

where

X is a vinyl group copolymerizable with the A and B monomers;

Y is a polyvalent linking group (e.g., alkylene, arylene, alkarylene, and aralkylene of 1 to 30 carbon atoms) optionally incorporating heteroatoms e.g. O, N, S, P. Examples are ester, amide, urethane, urea groups.

n is zero or 1;

$R^{12}$ is H or lower alkyl;

i is an integer from 0–2;

j is an integer from 1–3; and i+j=3;

T is a hydroxy or a hydrolyzable group that includes halogen atoms, alkoxy, alkenoxy, acyloxy, carboxy, amino, amido, dialkyliminooxy, ketoxime, aldoxime, and similar groups. Preferably, the hydrolyzable group is selected from the group consisting of alkoxy, alkenoxy, acyloxy, ketoxime and aldoxime. More preferably, the hydrolyzable groups are alkoxy groups such as methoxy and ethoxy, because of their commercial availability, low cost and low toxicity. Examples of such D units include, but not limited to, acrylato- and methacrylato-alkylalkoxysilanes as exemplified by the following formulae.

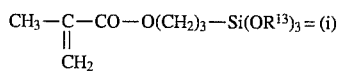
$$CH_3-\underset{CH_2}{\overset{\|}{C}}-CO-O(CH_2)_3-Si(OR^{13})_3 = (i)$$

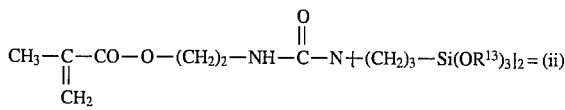
$$CH_3-\underset{CH_2}{\overset{\|}{C}}-CO-O-(CH_2)_2-NH-\overset{\overset{O}{\|}}{C}-N+(CH_2)_3-Si(OR^{13})_3]_2 = (ii)$$

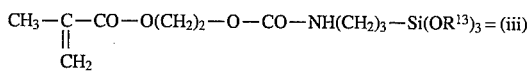
$$CH_3-\underset{CH_2}{\overset{\|}{C}}-CO-O(CH_2)_2-O-CO-NH(CH_2)_3-Si(OR^{13})_3 = (iii)$$

where, $R^{13}$ is lower alkyl.

Vinylorganoalkoxysilanes such as vinyltrimethoxysilane, vinyltriethoxysilane and vinyl tris(2-methoxyethoxy)silane may also be used in some instances.

These D unit compounds can be used in their unhydrolyzed, partially hydrolyzed, or fully hydrolyzed form. In the latter two forms, and particularly in the latter form, precautions must be taken to minimize the formation of gels by silane dimerization and oligomerization through siloxane bonds. Any method for this known to those skilled in the art can be used such as careful control of pH or capping of the hydroxyl groups to retard siloxane reactions.

The amount of the D unit silane compound used in the synthesis of the polymer described above preferably is such that the silane moiety is present in 0.1–30 mole percent of the polymer. More preferably, the silane moiety is present in 0.1–20 mole percent of the polymer, and most preferably in 0.1–10 mole percent of the polymer.

Copolymers containing a D unit as described above may be conveniently prepared by copolymerizing the starting monomer units A, B, C and D by standard vinyl polymerization techniques. Alternatively it is possible to modify a fraction of the polar groups of A of a prepared polymer with a compound having at least one silane moiety that is capable of undergoing a condensation reaction, which additionally has a group capable of reacting with the polar group of A.

Preferably, the coating composition contains three components. Component I is the copolymer containing a silane moiety that is capable of undergoing a condensation reaction as described above. Component II is a material having at least two condensation silicone reaction sites that are capable of undergoing a condensation reaction. Component III is optional catalyst to promote the condensation reaction between polymers of Component I and/or between polymers of Component I and compounds of Component II.

Component II is a compound having at least two condensation silicone reaction sites that are capable of undergoing a condensation reaction, and therefore acts as a bridging compound between polymers of Component I in the present system. This component may optionally be a comparatively small molecule, or may be polymeric in nature. Preferably, Component II has a weight average molecular weight between about 64–3000.

Examples of Component II include tetraethyl orthosilicate, and its partially or fully hydrolyzed forms. Preferably, Component II is described by the formula $$Y-[Si(R^{12})_iT_j]_k$$

where

Y is a polyvalent linking group (e.g., alkylene, arylene, alkarylene, and aralkylene of 1 to 30 carbon atoms) and optionally incorporating heteroatoms e.g. O, N, S, P. Examples are ester, amide, urethane, urea groups.

$R^{12}$ is H or lower alkyl i is an integer from 0–2 j is an integer from 1–3 i+j=3 k=2–50.

T is a hydroxy or a hydrolyzable group that includes halogen atoms, alkoxy, alkenoxy, acyloxy, carboxy, amino, amido, dialkyliminooxy, ketoxime, aldoxime, and similar groups. Preferably, the hydrolyzable group is selected from the group consisting of alkoxy, alkenoxy, acyloxy, ketoxime and aldoxime. More preferably, the hydrolyzable groups are alkoxy groups such as methoxy and ethoxy, because of their commercial availability, low cost and low toxicity.

Examples of Component II are as follows:

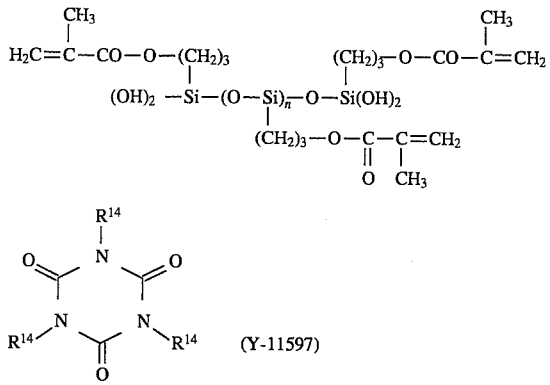

where $R^{14}=-(CH_2)_3-Si(OCH_3)_3$.

Component III is a catalyst that promotes the condensation of the silane moiety that is capable of undergoing a condensation reaction. Moisture generally favors such curing reactions. Any condensation silicone catalysts can be used for this purpose.

Preferred curing catalysts for crosslinking the polymers of the present coatings include the organometallic catalysts containing metals of group III-A, IV-A, V-A, VI-A, VIII-A, I-B, II-B, III-B, IV-B and V-B. Also preferred are the organic amine and organic acid catalysts for the silicone condensation reaction. Particularly preferred catalysts are tin dioctoate, tin naphthenate, dibutyltin dilaurate, dibutyltin diacetate, dibutyltin dioxide, dibutyl tin dioctoate, zirconium chelates, aluminum chelates, aluminum titanates, titanium isopropoxide, triethylene diamine, p-toluene sulfonic acid, n-butyl phosphoric acid, and mixtures thereof.

The combination of components I and III only, in the absence of II, may be sufficient to provide enough crosslinking for a particular application. On the other hand, in certain applications, it may be sufficient to combine components I and II only, particularly when component II is provided in a partially prehydrolyzed form. The speed of cure of the desired application, as well as the actual molecular architecture of the polymer of Component I and the bridging compound of Component II, will dictate the choice of a particular combination of the components of this invention. By judicious choice of solvents and packaging material and delivery system, it is possible to have a one-part or a multi-part system. In the latter case the multiple parts can be mixed just prior to application or can be applied as successive layers.

Polymers containing a silane moiety that is capable of undergoing a condensation reaction may be applied in the same manner as other polymers as described above. For example, these polymers may be applied to a surface of an article before insertion into the mouth, or may be polymerized in situ in the mouth on the oral surface. Coatings may additionally be treated with a surfactant-containing composition for additional benefit.

Coating of surfaces with compositions described herein after placement of orthodontic devices is particularly of interest. Protection of tooth surfaces adjacent to bonded brackets and the like is quite important because good oral hygiene is difficult and the orthodontic devices themselves provide interstices for bacteria, etc. to gather. An important method of use of the present coating materials is application after bonding of orthodontic devices to both the device itself and the tooth surface adjacent to the device.

In the method of the present invention, it is desirable to pretreat the oral surface to be coated with an acid before application of the coating composition. Suitable acids include citric acid, maleic acid, nitric acid, oxalic acid, the acids of phosphorous, sulfur, boron, and the like. Additionally, mildly acidic compositions such as those used to provide fluoride treatments may also be used with benefit as a oral surface pretreatment composition for surface preparation.

When the copolymer is applied as a coating it is generally useful to deliver it in combination with a carrier solvent. This carrier solvent is then removed by suitable means e.g. drying. Examples of carrier solvents include water, ethanol, isopropanol, acetone, silicone fluids such as $D_4$, and mixtures thereof. The coating can also be applied in the form of emulsion, e.g. oil-in-water or water-in-oil.

The coatings and surfactant treatments of this invention can be applied as an oral rinse or as a professionally applied coating that can be optionally fixed by further polymerization or cross-linking through ethylenic unsaturations present in the modulating group. The ingredients may also be incorporated into dentrifices such as toothpaste, dental gel, toothpowder, chewing gum, lozenges etc. The coatings and treatments may alternatively be part of a prophy paste or polishing paste that is then applied during a finishing or polishing process with prophy cup, angle, disc etc. They may also be applied by a floss for delivery to interproximal and other difficult to access areas.

For mouthwashes and mouthrinses, the liquid medium which acts as the carrier for the polymer or surfactant may be aqueous or aqueous alcoholic solutions, and optionally may contain other organic and inorganic solvents. For example, silicone fluids and fluorocarbon fluids of viscosity less than 100 cps may be used. A surfactant such as a detergent may be present in polymer delivery compositions.

Toothpastes, gels, chewing gum, lozenges and oral patches used for delivery of either the polymer or the surfactant may additionally contain humectants (such as glycerol, sorbitol, and polyethylene glycol), polishing agents (such as silica, calcium carbonate, and tricalcium phosphate), and thickeners (usually a natural or synthetic gum such as carrageenan, hydroxymethyl cellulose or a synthetic thickener such as fumed silica). A composition is defined to be a paste when the inelastic modulus is less than the elastic modulus of the composition. A composition is defined to be a gel when the inelastic modulus (otherwise known as loss modulus) is equal to the elastic modulus of the composition. The composition is considered to be "paintable" when it can be applied to the intended substrate using brushes, sponges or other applicators conventionally used in the dental arts.

Compositions for delivery of the polymer or surfactant may additionally contain other adjuvants, such as flavorants (both natural and synthetic, such as peppermint oil, menthol and sweeteners), coloring agents, viscosity modifiers, preservatives, antioxidants and antimicrobial agents (such as hydroquinone, BHT, ascorbic acid, p-hydroxybenzoic acid, alkyl esters, sodium sorbate and thymol), other anti-plaque additives (such as organophosphonates, triclosan and others such as those disclosed in U.S. Pat. No. 3,488,419), oral therapeutic agents (such as fluoride salts, chlorhexidine and allantoin), pigments and dyes and buffers to control ionic strength.

The compositions for delivery of the polymer may optionally additionally comprise an ethylenically unsaturated compound. Examples of preferred ethylenically unsaturated compounds are 2,2-bis[4-(2-hydroxy-3-methacryloxypropoxy)phenyl]propane "BIS-GMA") and 2-hydroxyethyl methacrylate "HEMA").

Polymers described herein are useful not only for incorporation into toothpastes and the like, but also may be used as external coating compositions for foreign devices to be placed temporarily or permanently in the mouth. For example, these coating compositions may be applied to dental articles that are manufactured outside of the mouth and subsequently placed in the mouth, such as orthodontic brackets, wires, bridges, crowns, dentures and the like. These compositions may be provided either before insertion into the mouth or after insertion by the dental practitioner or by the patient. When these coating compositions are applied to preexisting structure or man-made articles in the mouth, the coating composition may be applied in the form of the polymer or as precursors to the polymer which are in turn polymerized extra-orally or intra-orally by thermal, photoinitiated or redox polymerization. The low frictional coefficients of restorative materials coated by compositions containing these polymers improve the wear resistance of these restorations as compared to restoratives that do not contain these polymers.

When the polymers of the present compositions comprise pendant ethylenically unsaturated moieties that can be reacted in a subsequent step after application to the intended substrate, the compositions also comprise a polymerization catalyst to effect reaction of the ethylenically unsaturated group. Such catalyst may comprise a photoinitiation catalyst or the combination of an oxidizing agent and a reducing agent. Preferably, the initiation agent is appropriate from safety considerations for use in the human body.

The photoinitiator should be capable of promoting free radical crosslinking of the ethylenically unsaturated component on exposure to light of a suitable wavelength and intensity. It also preferably is sufficiently shelf-stable and free of undesirable coloration to permit its storage and use under typical dental conditions. Visible light photoinitiators are preferred. The photoinitiator frequently can be used alone but typically it is used in combination with a suitable donor compound or a suitable accelerator (for example, amines, peroxides, phosphorus compounds, ketones and alpha-diketone compounds).

Preferred visible light-induced initiators include camphorquinone (which typically is combined with a suitable hydrogen donor such as an amine), diaryliodonium simple or metal complex salts, chromophore-substituted halomethyl-s-triazines and halomethyl oxadiazoles. Particularly preferred visible light-induced photoinitiators include combinations of an alpha-diketone, e.g., camphorquinone, and a diaryliodonium salt, e.g., diphenyliodonium chloride, bromide, iodide or hexafluorophosphate, with or without additional hydrogen donors (such as sodium benzene sulfinate, amines and amine alcohols). Preferred ultraviolet light-induced polymerization initiators include ketones such as benzyl and benzoin, and acyloins and acyloin ethers. Preferred commercially available ultraviolet light-induced polymerization initiators include 2,2-dimethoxy-2-phenylacetophenone "IRGACURE 651") and benzoin methyl ether (2-methoxy-2-phenylacetophenone), both from Ciba-Geigy Corp.

The photoinitiator should be present in an amount sufficient to provide the desired rate of photopolymerization. This amount will be dependent in part on the light source and the extinction coefficient of the photoinitiator. Typically, the photoinitiator components will be present at a total weight of about 0.01 to about 5%, more preferably from about 0.1 to about 5%, based on the total weight (including water) of the unset coating components.

Alternative polymerization initiators include redox systems, which are a combination of a reducing agent and an oxidizing agent. These agents should react with or otherwise cooperate with one another to produce free-radicals capable of initiating polymerization of the ethylenically-unsaturated moiety. The reducing agent and oxidizing agent preferably are sufficiently shelf-stable and free of undesirable colorization to permit their storage and use under typical dental conditions. They should be sufficiently soluble in or miscible with the carrier medium. The reducing agent and oxidizing agent should be present in amounts sufficient to permit an adequate free-radical reaction rate. Useful reducing agent/oxidizing agent pairs are shown in "Redox Polymerization", G. S. Misra and U. D. N. Bajpai, *Prog. Polym. Sci.*, 8, 61–131 (1982).

Preferred reducing agents include ascorbic acid, cobalt (II) chloride, ferrous chloride, ferrous sulfate, hydrazine, aromatic and aliphatic amines hydroxylamine (depending upon the choice of oxidizing agent) oxalic acid, thiourea, sulfuric acids and salts, and salts of a dithionite or sulfite anion. Preferred oxidizing agents include cobalt (III) chloride, tert-butyl hydroperoxide, ferric chloride, hydroxylamine (depending upon the choice of reducing agent), perboric acid and its salts, and salts of a permanganate or persulfate anion. Hydrogen peroxide can also be used, although it has been found to interfere with the photoinitiator in some instances.

The amount of reducing agent and oxidizing agent should be sufficient to provide the desired degree of polymerization of the ethylenically-unsaturated component. The preferred amount for each of the reducing agent and oxidizing agent is about 0.01 to about 10%, more preferably about 0.02 to about 5%, based on the total weight (including water) of the components. Surfactant treatment, esp. neutral and cationic.

For crosslinkable polymers that are polymerized by a cationic mechanism, suitable intitators include salts that are capable of generating cations such as the diaryliodonium, triarylsulfonium and aryldiazonium salts.

As noted above, it has surprisingly been found that post-treatment of the coatings described herein by a surfactant containing composition may provide excellent reduction of adhesion for bacteria or proteinaceous materials. The surfactants may be incorporated at very small amounts in the post-coating composition, and may be either non-ionic or ionic surfactants. Particularly preferred surfactants for use in the post-coating treatment are non-ionic surfactants.

The preferred ionic surfactants include the salts of long-chained aliphatic acids such as sodium dodecylsulfate or sodium octadecyl sulfate. Optionally, the polymer of the coating may contain ionic functionality that acts as the counterion to the surfactant.

The preferred non-ionic surfactants are based on polyhydroxy esters of long chain fatty acids, or polyhydroxy ethers of long chain fatty alcohols. Particularly preferred are polyoxyethylene, sorbitan ethers of long chain fatty acids, e.g. Tween™ 20, 40, 60, or 80 surfactants.

Coatings as described herein may additionally be useful for coating medical articles and articles for use in the medical environment that would benefit from reduced adhesion to surfaces thereof. Examples of such medical articles include devices that are temporarily or permanently implanted in the body, such as pacemakers, blood vessel sieves, bone repair and replacement materials, and the like. Articles that come into contact with body fluids, such as catheters and surgical instruments, also may benefit from being provided with the coating of the present invention. Additionally, articles used for infection control purposes, such as gloves, masks, gowns, drapes and the like, may also benefit from the present coatings.

Substantivity of the coatings of the present invention may be measured by a number of techniques. For example, one may evaluate by chemical means whether or not a coating remains after other types of assault on the coatings. One such analytical means is evaluation of the advancing contact angle using a Wilhelmy Balance as described herein. Preferably, the contact angle is greater than 55°.

Alternatively, the continued effectiveness of the coating may be evaluated by determining resistance to stain or resistance to bacterial adhesion of a substrate. Resistance of the coating may be evaluated by using a physical assault or a soak assault on the coating. The physical assault may be provided by scrubbing with a brush having a predetermined load for limited periods of time. Alternatively, a physical assault may be provided by repetitious grinding or polishing of teeth under a mechanical mechanism used to simulate the action of teeth in the mouth.

Preferably, the coatings of the present invention are sufficiently substantive to the intended substrate to provide an advancing contact angle of at least 55° as measured using the Wilhelmy Balance as described herein for a sample that has been subjected to 2 weeks of soaking in distilled water at 37° C. More preferably, an advancing contact angle of at least 55° is provided on a sample that has been so soaked for three months.

Wilhelmy Balance

To evaluate the hydrophobicity of the coatings of the present invention, the well-known Wilhelmy Balance technique is used to measure the advancing contact angle. This technique is discussed, for example, in "Wettability," John C. Berg, editor, Marcel Dekker, Inc., New York, 1993, pp 11–25. Measurement is taken on a continous coated sample. All contact angle measurements are done with water.

The following examples are given to illustrate, but not limit, the scope of this invention. Unless otherwise indicated, all pans and percentages are by weight, and all molecular weights are weight average molecular weight.

EXAMPLES

Example 1

Acrylic acid (6 g), iso-butyl methacrylate (26 g), and methacryloyl terminated polystyrene macromer "13KPSMA", Sartomer, West Chester, Pa.) (4 g) were charged into a three-necked round-bottom flask, along with 54 ml of n-propanol and 54 ml of ethyl acetate and 0.2 g of asobisisobutyronitrile ("AIBN") initiator. The flask was fitted with a stirring device, nitrogen inlet tube, condenser and thermometer. The reagents were deoxygenated by allowing dry nitrogen to bubble briskly through the stirred, homogeneous solution for 15 minutes. At the end of this time the nitrogen flow was reduced and switched from bubbling to blanketing conditions. The reaction mixture was heated at 60° C. with stirring, using an oil bath equipped with an electronic temperature controller. Heating was continued for 24 hours. The nitrogen blanket was then turned off, the resultant polymer solution cooled to room temperature, and the diluted with 50/50 n-propanol/ethyl acetate to yield a solution which contained 10% polymer. This polymer was termed "polymer A".

Example 2

Acrylic acid (6 g), iso-butyl methacrylate (24.7 g), and methacryloyl terminated polystyrene macromer (4 g), alkoxysilane monomer γ-methacryloxypropyltrimethoxysilane ("A-174", OSi Specialties, Inc.) (1.3 g) were charged into a three-necked round-bottom flask, along with 54 ml of isopropanol and 54 ml of ethyl acetate and 0.2 g of AIBN initiator. The flask was fitted with a stirring device, nitrogen inlet tube, condenser and thermometer. The reagents were deoxygenated by allowing dry nitrogen to bubble briskly through the stirred, homogeneous solution for 15 minutes. At the end of this time the nitrogen flow was reduced and switched from bubbling to blanketing conditions. The reaction mixture was heated at 60° C. with stirring, using an oil bath equipped with an electronic temperature controller. Heating was continued for 24 hours. The nitrogen blanket was then turned off, the resultant polymer solution cooled to room temperature, and the diluted with 50/50 isopropanol/ethyl acetate to yield a solution which contained 10% polymer. This polymer was termed "polymer B".

Example 3

Acrylic acid (6 g), iso-butyl methacrylate (24.7 g), dodecyl methacrylate (4 g), and A-174 (1.3 g) were charged into a three-necked round-bottom flask, along with 108 ml of n-propanol and 0.2 g of AIBN initiator. The flask was fitted with a stirring device, nitrogen inlet tube, condenser and thermometer. The reagents were deoxygenated by allowing dry nitrogen to bubble briskly through the stirred, homogeneous solution for 15 minutes. At the end of this time the nitrogen flow was reduced and switched from bubbling to blanketing conditions. The reaction mixture was heated at 60° C. with stirring, using an oil bath equipped with an electronic temperature controller. Heating was continued for 24 hours. The nitrogen blanket was then turned off, the resultant polymer solution cooled to room temperature, and the diluted with n-propanol to yield a solution which contained 10% polymer. This polymer was termed "polymer C".

Example 4

Acrylic acid (6.6 g), iso-butyl methacrylate (26 g), and dodecyl methacrylate (4 g) were charged into a three-necked round-bottom flask, along with 108 ml of dry 2-butanone solvent and 0.2 g of AIBN initiator. The flask was fitted with a stirring device, nitrogen inlet tube, condenser and thermometer. The reagents were deoxygenated by allowing dry nitrogen to bubble briskly through the stirred, homogeneous solution for 15 minutes. At the end of this time the nitrogen flow was reduced and switched from bubbling to blanketing conditions. The reaction mixture was heated at 60° C. with stirring, using an oil bath equipped with an electronic temperature controller. Heating was continued for 24 hours. The reaction mixture was then allowed to cool down to room temperature. Di-t-butylhydroxy toluene (BHT, 0.036 g) and dibutyl tin dilaurate (0.05 g) were added to the stirred reaction mixture. The nitrogen inlet tube was replaced by an air inlet tube and the reaction temperature raised to 40° C. Air was briskly bubbled into the reaction mixture, while a solution of 2-isocyanatoethyl methacrylate (IEM, 1.3 g) in 30 ml of dry 2-butanone was added dropwise to the reaction mixture. After the addition of the IEM soution was complete the reaction was allowed to proceed at 40° C. for an additional period of two hours. The resultant polymer solution was then allowed to cool down to room temperature and the diluted with 2-butanone to yield a solution which contained 10% of the polymer. This polymer was termed "polymer D". To the 10% solution of polymer D, diphenyliodonium hexaflourophosphate (0.05%) and camphorquinone (0.05%) were added to make the polymer crosslinkable in the presence of light. This polymer D solution was stored in an opaque container.

Example 5

The hydrophobicity of polymers A-D were characterized by the advancing contact angle of water. The advancing contact angle of water was measured in duplicate and averaged using the Wilhelmy plate technique with a plate immersion speed of 50 microns/sec. Polymer-coated glass plates (22×22 ×0.15 mm) were used as plates for the measurements. The glass plates were silane treated with A-174 prior to dip coating the plates in the polymer solutions (10%) so that the polymers would adequately adhere to the glass plates. Polymers B and C were characterized with and without the presence of a condensation catalyst (5% stannous octoate by the polymer weight). The glass plates coated with polymer D were light cured using a DENTACOLOR™ XS (Kulzer, Inc., Germany) light source for 180 sec. The advancing water contact angle of polymers A-D are shown in Table 1.

The advancing water contact angle of enamel and dentin was likewise determined using the Wilhelmy plate technique. Enamel and dentin plates were prepared from bovine incisors using the following procedure. The buccal surfaces of bovine incisors were polished with 120 and 600 grit silicon carbide wet/dry sand paper to reveal clean, flat enamel or dentin surfaces. The polished tooth surfaces were sectioned from the remainder of the tooth using a diamond saw to obtain approximately 1 mm disks of enamel or dentin polished on one side. Two enamel disks of similar size and shape were joined at their unpolished surfaces using SCOTCHBOND™ MULTIPURPOSE PLUS dental adhesive (3M) so that the polished surfaces were facing outwards. Likewise dentin disks were joined. These enamel and dentin sandwiches were cut with a diamond saw to give plates of dimensions of approximately 6×8 mm. The contact angles of water were measured using a plate immersion speed of 50 microns/sec. The advancing water contact angle of enamel and dentin was measured in replicate (at least twice) and the averages are shown in Table 1. The results in comparison to the polymers A-D show that polymers are more hydrophobic than bare, polished enamel and dentin.

TABLE 1

| Polymer | Condensation Catalyst | | Advancing Water Contact Angle |
| --- | --- | --- | --- |
| A |   | None | 93.48 |
| B | 1 | None | 91.28 |
|   | 2 | Yes | 93.72 |
| C | 1 | None | 94.83 |
|   | 2 | Yes | 95.24 |
| D |   | None | 92.54 |
| Enamel |   | None | 40.02 |
| Dentin |   | None | 53.83 |

Example 6

The toothbrush/toothpaste abrasion resistance of the polymers A-D on enamel was determined using the following procedure. Bovine incisors were potted in polymethyl methacrylate such that the buccal surfaces were raised above the potting material. The buccal surfaces were then polished with 120 and 600 grit silicon carbide wet/dry sand paper to reveal clean, flat enamel surfaces. To further clean the polished enamel surfaces, the enamel was acid etched with 10% citric acid in water for 15 sec, rinsed and dried. Solutions of the plaque resistant polymers (10%) were applied to the polished enamel surfaces with a small brush and allowed to air dry. Polymers B and C were characterized with and without the presence of a condensation catalyst (5% stannous octoate by the polymer weight). Teeth coated with polymer D were light cured using a DENTACOLOR™ XS (Kulzer, Inc., Germany) light source for 180 sec. The coated enamel samples were conditioned at 37° C., 97% RH in a humidity oven for 20 hours prior to brushing.

Each coated enamel surface was brushed with an ORAL B™ 35 Soft Straight toothbrush under a load of 140 g at a frequency of 50 cycles/min for ten minutes. The enamel surface and toothbrush were immersed in a slurry of 50/50 by weight CREST™ Regular Flavor toothpaste/distilled water during the brushing process.

After brushing the percentage of the polished enamel surface that remained coated with polymer was determined using the following staining procedure. The staining procedure involved etching the polished surface with 37% phosphoric acid for one second, rinsing, immersing the surface in a 0.2% aqueous solution of Acid Violet #17 (Aldrich Chemical Company, Inc., Milwaukee, Wis.) for approximately 30 sec, rinsing, and drying. The phosphoric acid etching step demineralized any exposed enamel to a sufficient extent as to allow the uptake of the Acid Violet #17 dye. The plaque resistant polymers, however, are relatively unaffected by the phosphoric acid etching step and are resistant to staining with Acid Violet #17. Therefore, the percentage of the polished surface area that remained coated after brushing was determined by the percentage of the surface that was unstained. The percentage was determined by visual examination.

Table 2 shows the comparison of the toothbrush/toothpaste abrasion resistance of plaque resistant polymers A-D. The results shown are the average of at least two replicates. The results show that these polymer coatings have good resistance to abrasion encountered during tooth brushing.

TABLE 2

| Polymer | Condensation Catalyst | | Percentage of Area that Remained Coated After Brushing |
| --- | --- | --- | --- |
| A |   | None | 99.5 |
| B | 1 | None | 72.0 |
|   | 2 | Yes | 97.5 |
| C | 1 | None | 90.0 |
|   | 2 | Yes | 68.5 |
| D |   | None | 17.5 |

Example 7

The adherence of cariogenic bacteria to polymers A-D was determined using the following procedure. Clean bovine teeth were acid etched with 10% citric acid for 15 sec, rinsed and dried. The crowns of the acid etched teeth were then dip coated into 10% polymer solutions in 50/50 iso-propanol/acetone and allowed to air dry.

The polymer coated bovine teeth were placed in 10×30 mm polypropylene test tubes and held in place using 3M IMPRINT™ impressioning material. The teeth were placed such that only the crown area of the tooth was exposed. The teeth were then placed crown end down into the wells of a 24-well tissue culture plate (Costar, Inc., Cambridge, Mass.) and whole human saliva (2.3 ml) was added to each well to cover the crown. The teeth were incubated one hour with shaking at room temperature. "Mutans streptococci" (American Type Culture Collection, Rockville, Md.) washed in KCl buffer (0.1M NaCl, 0.05M KCl, 1 mM $KH_2PO_4$, 0.1 mM $MgCl_2$, 1 mM $CaCl_2$, pH 7.0) were added to the saliva ($10^9$ per tooth) and incubated an additional two hours at room temperature with shaking. The teeth were then washed twice with either KCl buffer or KCl buffer supplemented with 0.3% TWEEN-80 (Sigma, Inc., St. Louis, Mo.). The teeth were removed from the impressioning material and placed crown end down into new 24-well plates. KCl buffer or KCl buffer with TWEEN-80 (2 ml) was added to each well and the teeth washed twice more. DNA extraction buffer (0.4M NaOH, 10 mM ethylenediaminetetraacetic acid (EDTA)) (2.3 ml) was added to each well and the plates heated to 95°–100° C. for 12 minutes. The solubilized DNA was removed from the wells and divided into three equal portions. Each portion was added to the well of a slot-blot apparatus where the levels of bacterial DNA in each sample were determined. The teeth were then removed from the plates and numbered.

The level of bacterial DNA in each sample was determined using the following DNA slot-blot procedure. A sheet of Zeta-Probe hybridization membrane (BioRad Laboratories, Inc., Richmond, Calif.) was prepared by immersing the membrane in distilled water. The wet membrane was then mounted in a slot-blot apparatus (Minifold II, Schleicher & Schuell, Inc.), vacuum applied and each well rinsed with 0.5 ml of TE buffer (10 mM tris(hydroxymethyl)aminomethane hydrochloride (TRIZMA™ hydrochloride, Sigma, Inc.), 1 mM EDTA, pH 8.0). Solubilized DNA samples were added to each well and washed once with 0.4M NaOH. The vacuum source was disconnected after all liquid had been pulled through the membrane, the apparatus was disassembled and the DNA were immobilized on the semi-dry membrane by exposure to UV light for 3 minutes (StratLinker, Stratagene, Inc., LaJolla, Calif.). The membranes were rinsed briefly in 0.3M NaCl, 0.03M sodium citrate and dried in a 37° C. incubator. The dry membranes were placed in a glass hybridization chamber and 15 ml of pre-hybridization solution (Life Technologies, Inc, Grand Island, N.Y.) added. The tubes were rotated at 65° C. for one hour in the hybridization oven (Hybridizer 700, Stratagene, Inc.). Digoxegenin-labeled whole genomic probes for the organism being tested (150 ng) were added to pre-hybridization solution (15 ml). The diluted probes were boiled for 12 minutes. The pre-hybridization solution was then removed from the glass hybridization chambers and replaced by the diluted probe solution. The slot-blot was incubated overnight at 65° C. with the probe.

The slot-blot membranes incubated overnight with digoxigenin-labeled probes were removed from the hybridization oven and washed twice for 5 minutes in 0.3M NaCl, 0.03M sodium citrate with 0.1% sodium dodecyl sulphate (SDS) in a glass tray mounted on a shaker platform at room temperature. The membranes were washed twice in 50 ml of 15 mM NaCl, 1.5 mM sodium citrate with 0.1% SDS in the hybridization oven at 65° C. for 30 minutes. The membranes were then placed in a glass tray and washed for 2 minutes at room temperature in maleic acid buffer (0.15M NaCl, 0.1M maleic acid, pH 7.5). The membranes were incubated for 1 hour at room temperature in maleic acid buffer, with 10% skim milk proteins (KPL Laboratories, Gaithersburg, Md.) added, to block nonspecific reactant sites on the membrane. Anti-Digoxigenin antibody labeled with alkaline phosphatase (Boehringer Mannheim, Inc., Indianapolis, Ind.) was diluted 1:5000 in maleic acid buffer with 10% skim milk proteins and added to the membranes for 1 hour at room temperature. The antibody solution was removed and the membrane washed twice for 15 minutes in maleic acid buffer with 0.3% TWEEN-20. After removal of the wash buffer the membrane was equilibrated for 5 minutes in enzyme substrate buffer ( 0.1M TRIZMA hydrochloride, pH 9.5). Bromochloroindole phosphate/nitroblue tetrazolium enzyme substrate solution (KPL Laboratories, Inc.) was added and the membrane incubated in the dark at room temperature for 30 minutes. Color development was stopped by transfer of the membrane to TE buffer for 5 minutes followed by soaking in distilled water for 5–10 minutes. The membranes were then placed on paper towels to dry.

Dried membranes were placed on the transport tray of a densitometer (Model 325, Molecular Dynamics, Inc., Sunnyvale, Calif.) and scanned. The data was collected as a digital file using the Molecular Dynamics ImageQuant™ software. The net optical density of each slot was determined and compared to a standard curve of microbial DNA run on each membrane. The microbial equivalents of each slot was calculated and normalized by the tooth crown surface area determined by profilometry techniques.

The bacterial adherence results for polymers A-D are shown in Table 3 for two strains of "mutans streptococci" from the American Type Culture Collection (ATCC), Rockville, Md. The results shown in Table 3 are the percent reduction in bound Streptococcus sobrinus (ATCC 27351) and Streptococcus gordonii (ATCC 10558) compared to uncoated enamel. The two species of bacteria were evaluated with and without TWEEN-80 included in the KCl washes. When TWEEN-80 was included in the KCl washes of the polymer coated teeth, TWEEN-80 was also included in the KCl washes of the bare enamel control teeth. The results shown are the average of five replicate measurements. The results show that when the plaque resistance coatings were applied to enamel, a significant reduction in the binding of cariogenic bacteria was achieved.

TABLE 3

| Polymer | % Reduction in Adherence of ATCC 27351 | % Reduction in Adherence of ATCC 10558 | % Reduction in Adherence of ATCC 27351 with TWEEN-80 | % Reduction in Adherence of ATCC 10558 with TWEEN-80 | % Reduction in Adherence of ATCC 27351 with Stannous Octoate | % Reduction in Adherence of ATCC 10558 with Stannous Octoate |
|---|---|---|---|---|---|---|
| A | 54.11 | 70.62 | — | — | — | — |
| B | −25.36 | 9.40 | 100.00 | 84.69 | −41.65 | 61.79 |
| C | 79.18 | 87.16 | — | — | 99.98 | 93.34 |
| D | 82.96 | 64.55 | — | — | — | — |

What is claimed:

1. A coating on hard tissue surfaces or surfaces of the oral environment, which coating comprises a polymer that is less than 0.1 percent soluble in water comprising repeating units A) 1–80% by weight of a polar or polarizable group B) 0–98% by weight of a modulating group C) 1–40% by weight of a hydrophobic hydrocarbon moiety having a molecular weight greater than about 160, wherein said coating has a Wilhelmy Balance Test Advancing Contact Angle greater than 55°.

2. The coating of claim 1, wherein the C unit is 1–30% by weight of said polymer.

3. The coating of claim 1, wherein the polar or polarizable group is selected from the group consisting of hydroxy, thio, substituted and unsubstituted amido, cyclic ethers, phosphines, primary amines, secondary amines, tertiary amines, oxy acids of C, S, P, B, thiooxyacids of C, S, P, B, precursors and protected forms of these groups.

4. The coating of claim 1, wherein the A unit is derived from mono- or multifunctional carboxyl group-containing molecules represented by the general formula:

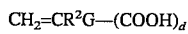

$$CH_2=CR^2G-(COOH)_d$$

where $R^2$=H, methyl, ethyl, cyano, carboxy or carboxymethyl, d=1–5 and G is a bond or a hydrocarbyl radical linking group containing from 1–12 carbon atoms of valence d+1 and optionally substituted and/or interrupted with a substituted or unsubstituted heteroatom, and salts thereof.

5. The coating of claim 4, wherein the A unit comprises a phosphorous-containing acid functionality.

6. The coating of claim 1, wherein the A unit is derived from mono- or multifunctional hydroxyl group-containing molecules represented by the general formula:

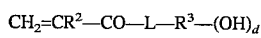

$$CH_2=CR^2-CO-L-R^3-(OH)_d$$

where $R^2$=H, methyl, ethyl, cyano, carboxy or carboxyalkyl, L=O, NH, d=1–5 and $R^3$ is a hydrocarbyl radical of valence d+1 containing from 1–12 carbon atoms.

7. The coating of claim 6, wherein the A unit is selected from the group consisting of hydroxyethyl (meth)acrylate, hydroxypropyl (meth)acrylate, hydroxybutyl (meth)acrylate, glycerol mono(meth)acrylate, tris(hydroxymethyl)ethane monoacrylate, pentaerythritol mono(meth)acrylate, N-hydroxymethyl (meth)acrylamide, hydroxyethyl (meth)acrylamide and hydroxypropyl (meth)acrylamide.

8. The coating of claim 1, wherein the A unit is selected from the group consisting of alkoxy substituted (meth)acrylates or (meth)acrylamides.

9. The coating of claim 1, wherein the A unit is derived from substituted or unsubstituted ammonium monomers of the general formula:

$$CH_2=CR^2-CO-L-R^3-(N^{\oplus}R^4R^5R^6)_dQ^-$$

where $R^2$=H, methyl, ethyl, cyano, carboxy or carboxyalkyl, L=O, NH, d=1–5 and $R^3$ a hydrocarbyl radical of valence d+1 containing from 1–12 carbon atoms and $R^4$ and $R^5$ are H or alkyl groups of 1–12 carbon atoms or together they constitute a carbocyclic or heterocyclic group, and where $R^6$ is H or alkyl of 1–30 carbon atoms and $Q^-$ is an organic or inorganic anion.

10. The coating of claim 1, wherein said coating additionally comprises at least one ethylenically unsaturated compound.

11. The coating of claim 10, wherein the ethylenically unsaturated compound is BIS-GMA.

12. The coating of claim 10, wherein the ethylenically unsaturated compound is HEMA.

13. A dental composition suitable for coating human oral surfaces, said composition comprising a polymer that is less than 0.1 percent soluble in water comprising repeating units A) 1–80% by weight of a polar or polarizable group B) 0–98% by weight of a modulating group C) 1–40% by weight of a hydrophobic hydrocarbon moiety having a molecular weight greater than about 160, wherein a coating of said polymer composition has a Wilhelmy Balance Test Advancing Contact Angle greater than 55°, wherein said polymer additionally contains at least one silane moiety that is capable of undergoing a condensation reaction.

14. The composition of claim 13, wherein the silane moiety is present in 0.1–30 mole percent of the polymer.

15. The composition of claim 13, wherein the silane moiety has the formula $$-Si(R^{12})_iT_j$$

where $R^{12}$ is H or lower alkyl;

i is an integer from 0–2;

j is an integer from 1–3;

i+j=3; and

T is hydroxy or a hydrolyzable group selected from the group consisting of halogen atoms, alkoxy, alkenoxy, acyloxy, carboxy, amino, amido, dialkyliminooxy, ketoxime, and aldoxime.

16. A dental composition suitable for coating human oral surfaces, said composition comprising a polymer that is less than 0.1 percent soluble in water comprising repeating units A) 1–80% by weight of a polar or polarizable group, B) 0–98% by weight of a modulating group, C) 1–40% by weight of a hydrophobic hydrocarbon moiety having a molecular weight greater than about 160, wherein a coating of said polymer composition has a Wilhelmy Balance Test Advancing Contact Angle greater than 55°, D) 1–50% by weight of a group having the formula $$X(Y)n-Si(R^{12})_iT_j$$

where

X is a vinyl group copolymerizable with the A and B monomers;

Y is a polyvalent linking group;

n is zero or 1;

$R^{12}$ is H or lower alkyl;

i is an integer from 0–2;

j is an integer from 1–3;

i+j=3; and

T is a hydroxy or a hydrolyzable group selected from the group consisting of halogen atoms, alkoxy, alkenoxy, acyloxy, carboxy, amino, amido, dialkyliminooxy, ketoxime and aldoxime.

17. The composition of claim 16, wherein T is selected from the group consisting of alkoxy, alkenoxy, acyloxy, ketoxime and aldoxime.

18. The composition of claim 16, wherein T is an alkoxy group.

19. The composition of claim 15, said composition additionally comprising a catalyst that promotes the condensation of reactive silane moieties.

20. The composition of claim 19, wherein said catalyst is selected from the group consisting of organometallic catalysts containing metals of group III-A, IV-A, V-A, VI-A, VIII-A, I-B, II-B, III-B, IV-B and V-B.

21. The composition of claim 20, wherein said catalyst is selected from the group consisting of tin dioctoate, tin naphthenate, dibutyltin dilaurate, dibutyltin diacetate, dibutyltin dioxide, dibutyl tin dioctoate, zirconium chelates, aluminum chelates, aluminum titanates, titanium isopropoxide and mixtures thereof.

22. The composition of claim 19, wherein said catalyst is selected from the group consisting of triethylene diamine, p-toluene sulfonic acid, n-butyl phosphoric acid, and mixtures thereof.

23. The composition of claim 19, said composition additionally comprising a compound comprising at least two condensation silicone reaction sites that are capable of undergoing a condensation reaction.

24. The composition of claim 23, wherein said compound has the formula $$Y-[Si(R^{12})_iT_j]_k$$

where

Y is a polyvalent linking group;

$R^{12}$ is H or lower alkyl;

i is an integer from 0–2;

j is an integer from 1–3;

i+j=3;

k=2–50; and

T is a hydroxy or a hydrolyzable group selected from the group consisting of halogen atoms, alkoxy, alkenoxy, acyloxy, carboxy, amino, amido, dialkyliminooxy, ketoxime and aldoxime.

25. The composition of claim 24, wherein T is selected from the group consisting of alkoxy, alkenoxy, acyloxy, ketoxime and aldoxime.

26. The composition of claim 24, wherein T is an alkoxy group.

27. The composition of claim 23, wherein said compound has the formula

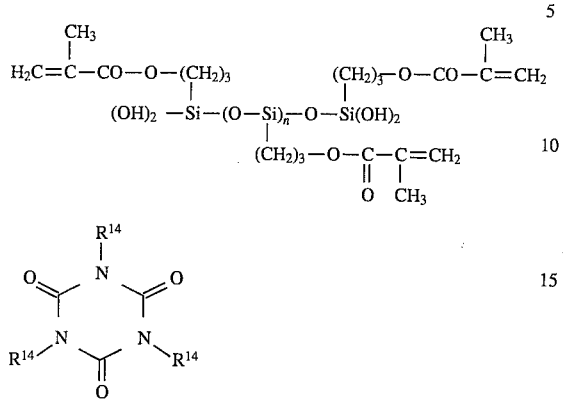

where $R^{14}=-(CH_2)_3-Si(OCH_3)_3$.

28. The composition of claim 23, said composition additionally comprising a catalyst that promotes the condensation of reactive silane moieties.

29. The composition of claim 28, wherein said catalyst is selected from the group consisting of organometallic catalysts containing metals of group III-A, IV-A, V-A, VI-A, VIII-A, I-B, II-B, III-B, IV-B and V-B.

30. The composition of claim 29, wherein said catalyst is selected from the group consisting of tin dioctoate, tin naphthenate, dibutyltin dilaurate, dibutyltin diacetate, dibutyltin dioxide, dibutyl tin dioctoate, zirconium chelates, aluminum chelates, aluminum titanates, titanium isopropoxide and mixtures thereof.

31. The composition of claim 28, wherein said catalyst is selected from the group consisting of triethylene diamine, p-toluene sulfonic acid, n-butyl phosphoric acid, and mixtures thereof.

32. The composition of claim 13, wherein said polymer has a weight average molecular weight between 10,000–10,000,000.

33. The composition of claim 13, wherein said polymer has a weight average molecular weight between 50,000–5,000,000.

* * * * *